(12) United States Patent
Watanabe

(10) Patent No.: US 6,436,983 B1
(45) Date of Patent: Aug. 20, 2002

(54) TREATMENT FOR ALZHEIMER'S DISEASE

(75) Inventor: August M Watanabe, Carmel, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 09/529,247

(22) PCT Filed: Nov. 14, 1998

(86) PCT No.: PCT/US98/24234

§ 371 (c)(1),
(2), (4) Date: Apr. 10, 2000

(87) PCT Pub. No.: WO99/25339

PCT Pub. Date: May 27, 1999

Related U.S. Application Data

(60) Provisional application No. 60/066,036, filed on Nov. 14, 1997.

(51) Int. Cl.[7] .............................................. A61K 31/40
(52) U.S. Cl. ..................................................... 514/419
(58) Field of Search ................................. 514/419, 493

(56) References Cited

U.S. PATENT DOCUMENTS 5,654,326 A * 8/1997 Bach et al. .................. 514/419

* cited by examiner

Primary Examiner—Theodore J. Criares
(74) Attorney, Agent, or Firm—Roger S. Benjamin

(57) ABSTRACT

This invention is a method of treating a mammal, including a human, susceptible to having Alzheimer's disease, to prevent or delay the onset of Alzheimer's disease; said method comprising administering to said mammal a prophylactically effective amount of 1H-indole-3-glycoxyamide sPLA$_2$ inhibitor or a pharmaceutically acceptable salt, solvate or prodrug derivative thereof.

7 Claims, No Drawings

TREATMENT FOR ALZHEIMER'S DISEASE

This application claims the benefit of Provisional Application No. 60/066,036 filed Nov. 14, 1997.

BACKGROUND OF THE INVENTION

Alzheimer's disease is a degenerative disorder of the human brain. Clinically, it appears as a progressive dementia. Its histopathology is characterized by degeneration of neurons, gliosis, and the abnormal deposition of proteins in the brain. Pathological hallmarks include neurofibrillary tangles (paired helical filaments) and amyloid deposits within the parenchyma and cerebral vasculature.

Recent studies indicate that a major component of the pathology of Alzheimer's disease is chronic inflammation. See, J. Schnabel, Science, 260:1719–1720 (1993). Administration of nonsteroidal anti-inflammatory drugs appears to slow the advance of Alzheimer's disease. Understanding this inflammatory component of Alzheimer's disease may lead to advances in methods of treating patients suffering from this disease.

The structure and physical properties of human non-pancreatic secretory phospholipase $A_2$ (hereinafter called, "$sPLA_2$") has been described in two articles, namely, "Cloning and Recombinant Expression of Phospholipase $A_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; The Journal of Biological Chemistry, Vol. 264, No. 10, Issue of April 5, pp. 5335–5338, 1989; and "Structure and Properties of a Human Non-pancreatic Phospholipase $A_2$" by Kramer, Ruth M.; Hession, Catherine; Johansen, Berit; Hayes, Gretchen; McGray, Paula; Chow, E. Pingchang; Tizard, Richard; and Pepinsky, R. Blake; The Journal of Biological Chemistry, Vol. 264, No. 10, Issue of April 5, pp. 5768–5775, 1989; the disclosures of which are incorporated herein by reference.

It is believed that $sPLA_2$ is a rate limiting enzyme in the arachidonic acid cascade which hydrolyzes membrane phospholipids.

The scientific literature suggests NSAIDs may be beneficial in the treatment of Alzheimer's Disease. Moreover, COX-2 inhibitors are currently being tested for treatment of Alzheimer's.

$PLA_2$ inhibitors have been proposed as treatment for Alzheimer's disease (see, U.S. Pat. No. 5,478,857), but tykpically these have been cytosolic phospholipase $A_2$ inhibitors.

Because of the debilitating effects of Alzheimer's disease there continues to exist a need for effective treatments. This invention provides methods for the treatment of Alzheimer's disease in mammals.

SUMMARY OF THE INVENTION

This invention is a method of treating a mammal, including a human, susceptible to having Alzheimer's disease, to prevent or delay the onset of Alzheimer's disease; said method comprising administering to said mammal a prophylactically effective amount of 1H-indole-3-glyoxylamide $sPLA_2$ inhibitor or a pharmaceutically acceptable salt, solvate or prodrug derivative thereof.

This invention is also a method of treating a mammal, including a human, already afflicted with Alzheimer's disease to prevent or diminish the rate of further deterioration; said method comprising administering to said mammal a therapeutically effective amount of 1H-indole-3-glyoxylamide compound or a pharmaceutically acceptable salt, solvate or prodrug derivative thereof.

DETAILED DESCRIPTION AND PREFERRED EMBODIMENTS

All temperatures stated herein are in degrees Celsius (°C.). All units of measurement employed herein are in weight units except for liquids which are in volume units.

General Definitions

The term "prophylactically effective amount" is the quantity of 1H-indole-3-glyoxylamide $sPlA_2$ inhibitor required to prevent or significantly delay the onset of Alzheimer's disease in a mammal susceptible (by reason of age, family history, etc.) to contracting Alzheimer's disease.

The term "therapeutically effective amount" is the quantity of 1H-indole-3-glyoxylamide $sPLA_2$ inhibitor sufficient to prevent or retard the progress of Alzheimer's disease in a mammal already afflicted with Alzheimer's disease.

The term "parenteral" means not through the alimentary canal but by some other route such as subcutaneous, intramuscular, intraorbital, intracapsular, intraspinal, intrasternal, or intravenous.

The term "active compound" means one or more $sPLA_2$ inhibitors used in the method of the invention as further described in Formula I or named below.

I. $sPLA_2$ Inhibitors Useful in the Method of the Invention

The 1H-indole-3-glyoxylamide $sPLA_2$ inhibitors and method of making them are described in U.S. Pat. No. 5,654,326, the entire disclosure of which is incorporated herein by reference. Another method of making 1H-indole-3-glyoxylamide $sPLA_2$ inhibitors is described in U.S. patent application Ser. No. 09/105,381, filed Jun. 26, 1998 and titled, "Process for Preparing 4-substituted 1-H-Indole-3-glyoxyamides" the entire disclosure of which is incorporated herein by reference. U.S. patent application Ser. No. 09/105381 discloses the following process having steps (a) thru (i):

Preparing a compound of the formula I or a pharmaceutically acceptable salt or prodrug derivative thereof

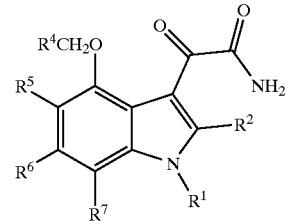

(I)

wherein:

$R^1$ is selected from the group consisting of —$C_7$—$C_{20}$ alkyl,

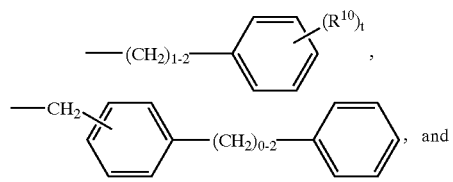

-continued

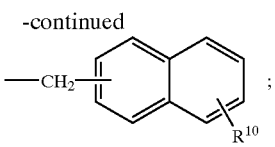

where
R¹⁰ is selected from the group consisting of halo, $C_1-C_{10}$ alkyl, $C_1-C_{10}$ alkoxy, —S—($C_1-C_{10}$ alkyl) and halo($C_1-C_{10}$)alkyl, and t is an integer from 0 to 5 both inclusive;

R² is selected from the group consisting of hydrogen, halo, $C_1-C_3$ alkyl, $C_3-C_4$ cycloalkyl, $C_3-C_4$ cycloalkenyl, —O—($C_1-C_2$ alkyl), —S—($C_1-C_2$ alkyl), aryl, aryloxy and HET;

R⁴ is selected from the group consisting of —CO₂H, —SO₃H and —P(O)(OH)₂ or salt and prodrug derivatives thereof; and R⁵, R⁶ and R⁷ are each independently selected from the group consisting of hydrogen, ($C_1-C_6$)alkyl, ($C_1-C_6$) alkoxy, halo($C_1-C_6$)alkoxy, halo($C_2-C_6$)alkyl, bromo, chloro, fluoro, iodo and aryl;

which process comprises the steps of:
a) halogenating a compound of formula X

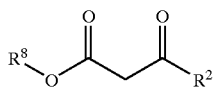

where R⁸ is ($C_1-C_6$)alkyl, aryl or HET; with SO₂Cl₂ to form a compound of formula IX

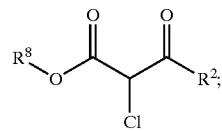

b) hydrolyzing and decarboxylating a compound of formula IX

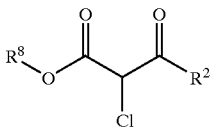

to form a compound of formula VIII

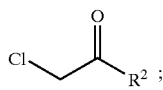

c) alkylating a compound of formula VII

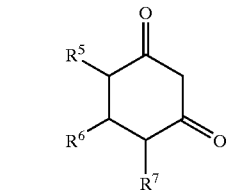

with a compound of formula VIII

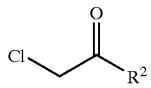

to form a compound of formula VI

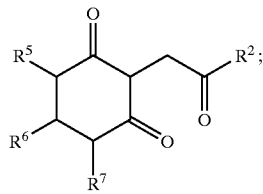

d) aminating and dehydrating a compound of formula VI

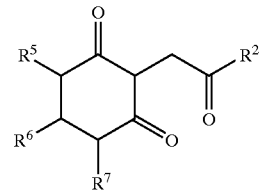

with an amine of the formula R¹NH₂ in the presence of a solvent that forms and azeotrope with water to form a compound of formula V;

e) oxidizing a compound of formula V

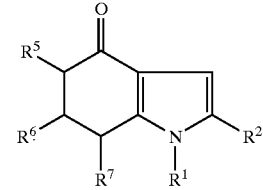

by refluxing in a polar hydrocarbon solvent having a boiling point of at least 150° C. and a dielectric constant of at least 10 in the presence of a catalyst to form a compound of formula IV

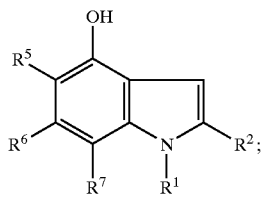

f) alkylating a compound of the formula IV

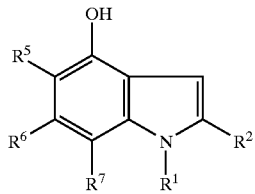

with an alkylating agent of the formula $XCH_2R^{4a}$ where X is a leaving group and $R^{4a}$ is $—CO_2R^{4b}$, $—SO_3R^{4b}$, $—P(O)(OR^{4b})_2$, or $—P(O)(OR^{4b})H$, where $R^{4b}$ is an acid protecting group to form a compound of formula III

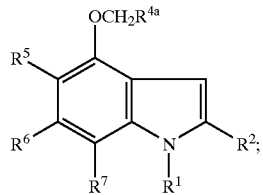

g) reacting a compound of formula III

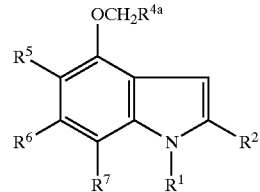

with oxalyl chloride and ammonia to form a compound of formula II

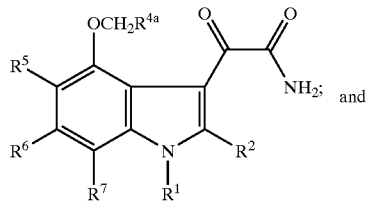

and h) optionally hydrolyzing a compound of formula II

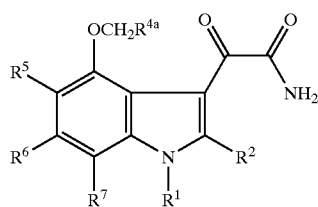

to form a compound of formula I; and i) optionally salifying a compound of formula I.

The synthesis methodology for making the 1H-indole-3-glyoxylamide sPLA$_2$ inhibitor starting material may be by any suitable means available to one skilled in the chemical arts. However, such methodology is not part of the present invention which is a method of use, specifically, a method of treating mammal afflicted with or susceptible to Alzheimer's Disease.

The method of the invention is for treatment of a mammal, including a human, afflicted with Alzheimer's Disease, said method comprising administering to said human a therapeutically effective amount of the compound represented by formula (Ia), or a pharmaceutically acceptable salt or prodrug derivative thereof;

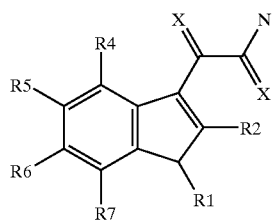

wherein both X are oxygen;

$R_1$ is selected from the group consisting of

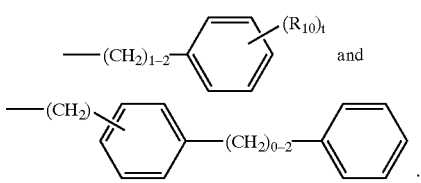

where $R_{10}$ is a radical independently selected from halo, $C_1–C_{10}$ alkyl, $C_1–C_{10}$ alkoxy, $—S—(C_1–C_{10}$ alkyl), and $C_1–C_{10}$ haloalkyl and t is a number from 0 to 5;

$R_2$ is selected from the group; halo, cyclopropyl, methyl, ethyl, and propyl;

$R_4$ and $R_5$ are independently selected from hydrogen, a non-interfering substituent, or the group, $—(L_a)$-(acidic group); wherein $—(L_a)—$ is an acid linker; provided, the acid linker group, $—(L_a)—$, for $R_4$ is selected from the group consisting of;

$—[O—CH_2]—$, $—[S—CH_2]—$, $—[N—CH_2]—$,

-continued

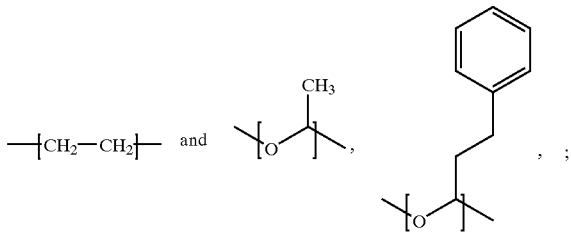

and provided, the linker, —(L$_a$)—, for R$_5$ is selected from the group consisting of;

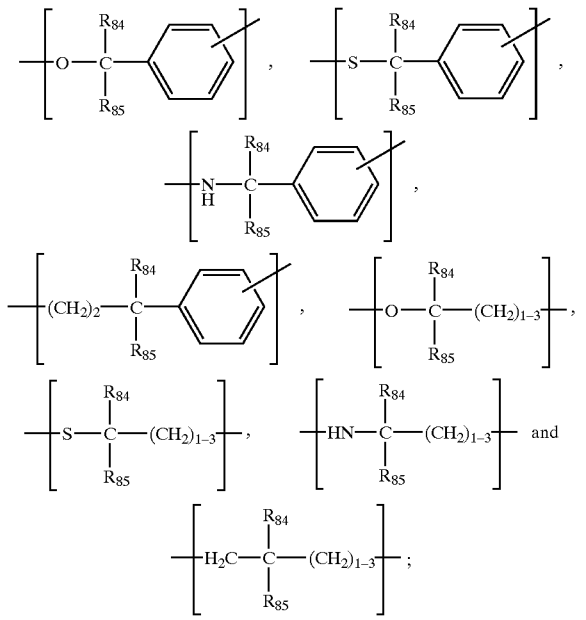

wherein R$_{84}$ and R$_{85}$ are each independently selected from hydrogen, C$_1$–C$_{10}$ alkyl, aryl, C$_1$–C$_{10}$ alkaryl, C$_1$–C$_{10}$ aralkyl, carboxy, carbalkoxy, and halo; and provided, that at least one of R$_4$ and R$_5$ must be the group, —(L$_a$)-(acidic group) and wherein the (acidic group) on the group —(L$_a$)-(acidic group) of R$_4$ or R$_5$ is selected from —CO$_2$H, —SO$_3$H, or —P(O)(OH)$_2$;

R$_6$ and R$_7$ are each independently selected form hydrogen and non-interfering substituents, with the non-interfering substituents being selected from the group consisting of the following: C$_1$–C$_6$ alkyl, C$_2$–C$_6$ alkenyl, C$_2$–C$_6$ alkynyl, C$_7$–C$_{12}$ aralkyl, C$_7$–C$_{12}$ alkaryl, C$_3$–C$_8$ cycloalkyl, C$_3$–C$_8$ cycloalkenyl, phenyl, tolulyl, xylenyl, biphenyl, C$_1$–C$_6$ alkoxy, C$_2$–C$_6$ alkenyloxy, C$_2$–C$_6$ alkynyloxy, C$_2$–C$_{12}$ alkoxyalkyl, C$_2$–C$_{12}$ alkoxyalkyloxy, C$_2$–C$_{12}$ alkylcarbonyl, C$_2$–C$_{12}$ alkylcarbonylamino, C$_2$–C$_{12}$ alkoxyamino, C$_2$–C$_{12}$ alkoxyaminocarbonyl, C$_2$–C$_{12}$ alkylamino, C$_1$–C$_6$ alkylthio, C$_2$–C$_{12}$ alkylthiocarbonyl, C$_1$–C$_6$ alkylsulfinyl, C$_1$–C$_6$ alkylsulfonyl, C$_2$–C$_6$ haloalkoxy, C$_1$–C$_6$ haloalkylsulfonyl, C$_2$–C$_6$ haloalkyl, C$_1$–C$_6$ hydroxyalkyl, —C(O)O(C$_1$–C$_6$ alkyl), (CH$_2$)$_n$—O—(C$_1$–C$_6$ alkyl), benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and C$_1$–C$_6$ carbonyl; where n is from 1 to 8.

Preferred for practicing the method of the invention are 1H-indole-3-glyoxylamide compounds and all corresponding pharmaceutically acceptable salts, solvates and prodrug derivatives thereof which are useful in the method of the invention include the following:

(A) [[3-(2-Amino-1,2-dioxoethyl)-2-methyl-1-(phenylmethyl)-1H-indol-4-yl]oxy]acetic acid,
(B) d-2-[[3-(2-Amino-1,2-dioxoethyl)-2-methyl-1-(phenylmethyl)-1H-indol-4-yl]oxy]propanoic acid,
(C) [[3-(2-Amino-1,2-dioxoethyl)-1-([1,1'-biphenyl]-2-ylmethyl)-2-methyl-1H-indol-4-yl]oxy]acetic acid,
(D) [[3-(2-Amino-1,2-dioxoethyl)-1-([1,1'-biphenyl]-3-ylmethyl)-2-methyl-1H-indol-4-yl]oxy]acetic acid,
(E) [[3-(2-Amino-1,2-dioxoethyl)-1-([1,1'-biphenyl]-4-ylmethyl)-2-methyl-1H-indol-4-yl]oxy]acetic acid,
(F) [[3-(2-Amino-1,2-dioxoethyl)-1-[(2,6-dichlorophenyl)methyl]-2-methyl-1H-indol-4-yl]oxy]acetic acid
(G) [[3-(2-Amino-1,2-dioxoethyl)-1-[4(-fluorophenyl)methyl]-2-methyl-1H-indol-4-yl]oxy]acetic acid,
(H) [[3-(2-Amino-1,2-dioxoethyl)-2-methyl-1-[(1-naphthalenyl)methyl]-1H-indol-4-yl]oxy]acetic acid,
(I) [[3-(2-Amino-1,2-dioxoethyl)-2-ethyl-1-(phenylmethyl)-1H-indol-4-yl]oxy]acetic acid,
(J) [[3-(2-Amino-1,2-dioxoethyl)-1-[(3-chlorophenyl)methyl]-2-ethyl-1H-indol-4-yl]oxy]acetic acid,
(K) [[3-(2-Amino-1,2-dioxoethyl)-1-([1,1'-biphenyl]-2-ylmethyl)-2-ethyl-1H-indol-4-yl]oxy]acetic acid,
(L) [[3-(2-amino-1,2-dioxoethyl)-1-([1,1'-biphenyl]-2-ylmethyl)-2-propyl-1H-indol-4-yl]oxy]acetic acid,
(M) [[3-(2-Amino-1,2-dioxoethyl)-2-cyclopropyl-1-(phenylmethyl)-1H-indol-4-yl]oxy]acetic acid,
(N) [[3-(2-Amino-1,2-dioxoethyl)-1-([1,1'-biphenyl]-2-ylmethyl)-2-cyclopropyl-1H-indol-4-yl]oxy]acetic acid,
(O) 4-[[3-(2-Amino-1,2-dioxoethyl)-2-ethyl-1-(phenylmethyl)-1H-indol-5-yl]oxy]butanoic acid,
(P) mixtures of (A) through (P) in any combination.

Particularly useful prodrugs of the compounds of formula (I) and named compounds (A) thru (O) are the simple aromatic and aliphatic esters, such as the methyl ester, ethyl ester, n-propyl ester, isopropyl ester, n-butyl ester, sec-butyl, tert-butyl ester, N,N-diethylglycolamido ester, and morpholino-N-ethyl ester. Methods of making ester prodrugs are disclosed in U.S. Pat. No. 5,654,326. Additional methods of prodrug synthesis are disclosed in U.S. Provisional Patent Application Serial No. 60/063280 filed Oct. 27, 1997 (titled, N,N-diethylglycolamido ester Prodrugs of Indole sPLA2 Inhibitors), the entire disclosure of which is incorporated herein by reference; U.S. Provisional Patent Application Serial No. 60/063646 filed Oct. 27, 1997 (titled, Morpholino-N-ethyl Ester Prodrugs of Indole sPLA2 Inhibitors), the entire disclosure of which is incorporated herein by reference; and U.S. Provisional Patent Application Serial No. 60/063284 filed Oct. 27, 1997 (titled, Isopropyl Ester Prodrugs of Indole sPLA$_2$ Inhibitors), the entire disclosure of which is incorporated herein by reference.

Most preferred in the practice of the method of the invention are the acid, sodium salt, methyl ester, and morpholino-N-ethyl ester forms of [[3-(2-Amino-1,2-dioxoethyl)-2-ethyl-1-(phenylmethyl)-1H-indol-4-yl]oxy] acetic acid as represented by the following formulae:

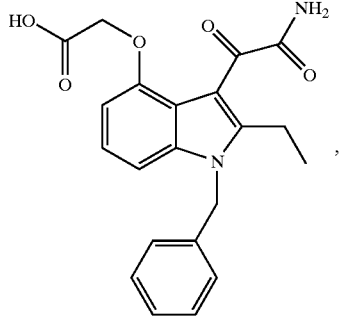
,
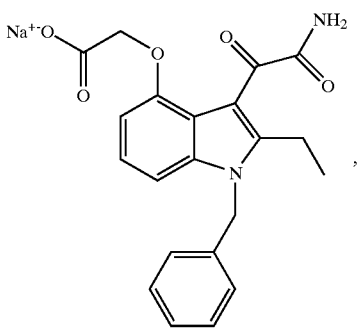
, and
Another highly preferred compound is the indole-3-glyoxylamide morpholino ethyl ester of represented by the formula:
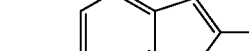
;
the preparation of which is further described in U.S. provisional patent application Serial No. 60/063,646 filed Oct. 27, 1997.
Synthesis methods for 1H-indole-3-glyoxylamide sPLA$_2$ inhibitors are additionally depicted in the following reaction scheme:
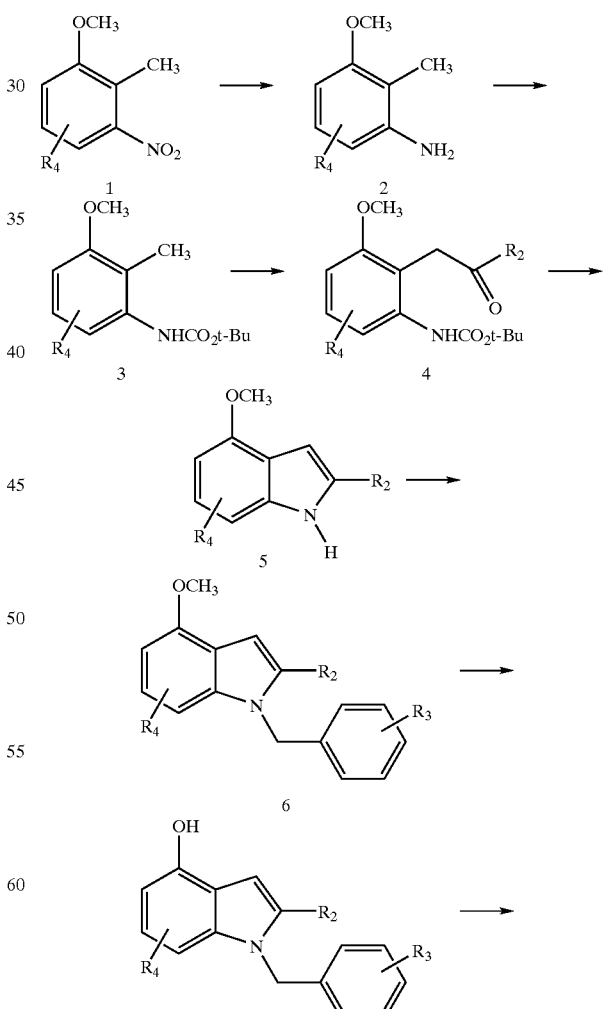

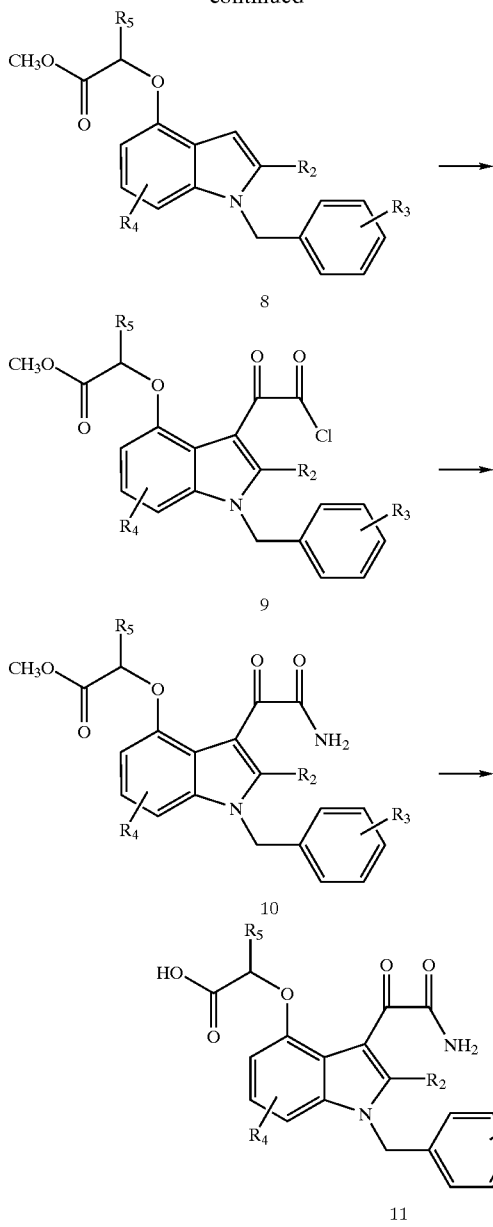

Explanation of Reaction Scheme

To obtain the glyoxylamides substituted in the 4-position with an acidic function through an oxygen atom, the reactions outlined in scheme 1 are used (for conversions 1 through 5, see ref. Robin D. Clark, Joseph M. Muchowski, Lawrence E. Fisher, Lee A. Flippin, David B. Repke, Michel Souchet, *Synthesis,* 1991, 871–878, the disclosures of which are incorporated herein by reference). The ortho-nitrotoluene, 1, is readily reduced to the 2-methylaniline, 2, using Pd/C as catalyst. The reduction can be carried out in ethanol or tetrahydrofuran (THF) or a combination of both, using a low pressure of hydrogen. The aniline, 2, on heating with di-tert-butyl dicarbonate in THF at reflux temperature is converted to the N-tert-butylcarbonyl derivative, 3, in good yield. The dilithium salt of the dianion of 3 is generated at −40 to −20° C. in THF using sec-butyl lithium and reacted with the appropriately substituted N-methoxy-N-methylalkanamide. This product, 4, may be purified by crystallization from hexane, or reacted directly with trifluoroacetic acid in methylene chloride to give the 1,3-unsubstituted indole 5. The 1,3-unsubstituted indole 5 is reacted with sodium hydride in dimethylformamide at room temperature (20–25° C.) for 0.5–1.0 hour. The resulting sodium salt of 5 is treated with an equivalent of arylmethyl halide and the mixture stirred at a temperature range of 0–100° C., usually at ambient room temperature, for a period of 4 to 36 hours to give the 1-arylmethylindole, 6. This indole, 6, is O-demethylated by stirring with boron tribromide in methylene chloride for approximately 5 hours (see ref. Tsung-Ying Shem and Charles A Winter, Adv. Drug Res., 1977, 12, 176, the disclosure of which is incorporated herein by reference). The 4-hydroxyindole, 7, is alkylated with an alpha bromoalkanoic acid ester in dimethylformamide (DMF) using sodium hydride as a base, with reactions conditions similar to that described for the conversion of 5 to 6. The a-[(indol-4-yl)oxy]alkanoic acid ester, 8, is reacted with oxalyl chloride in methylene chloride to give 9, which is not purified but reacted directly with ammonia to give the glyoxamide 10. This product is hydrolyzed using 1N sodium hydroxide in MeOH. The final glyoxylamide, 11, is isolated either as the free carboxylic acid or as its sodium salt or in both forms.

The most preferred compound, [[3-(2-Amino-1,2-dioxoethyl)-2-ethyl-1-(phenylmethyl)-1H-indol-4-yl]oxy] acetic acid (as well as its sodium salt and methyl ester) useful in the practice of the method of the invention, may be prepared by the following procedure:

Preparation of [[3-(2-Amino-1,2-dioxoethyl)-2-ethyl-1-(phenylmethyl)-1H-indol-4-yl]oxy]acetic acid, a compound represented by the formula:

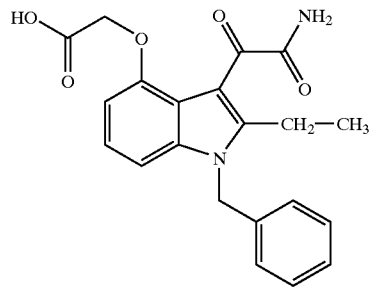

Part A. Preparation of 2-Ethyl-4-methoxy-1H-indole

A solution of 140 mL (0.18 mol) of 1.3M sec-butyl lithium in cyclohexane is added slowly to N-tert-butoxycarbonyl-3-methoxy-2-methylaniline (21.3 g, 0.09 mol) in 250 mL of THF keeping the temperature below −40° C. with a dry ice-ethanol bath. The bath is removed and the temperature allowed to rise to 0° C. and then the bath replaced. After the temperature has cooled to −60° C., 18.5 g (0.18 mmol) of N-methoxy-N-methylpropanamide in an equal volume of THF iss added dropwise. The reaction mixture is stirred 5 minutes, the cooling bath removed and stirred an additional 18 hours. It is then poured into a mixture of 300 mL of ether and 400 mL of 0.5N HCl. The organic layer is separated, washing with water, brine, dried over MgSO$_4$, and concentrated at reduced pressure to give 25.5 g of a crude of 1-[2-(tert-butoxycarbonylamino)-6-methoxyphenyl]-2-butanone. This material is dissolved in 250 mL of methylene chloride and 50 mL of trifluoroacetic acid and stirred for a total of 17 hours. The mixture is concentrated at reduced pressure and ethyl acetate and water added to the remaining oil. The ethyl acetateis separated, washed with brine, dried (MgSO$_4$) and concentrated. The residue is chromatographed three times on silica eluting with 20% EtOAc/hexane to give 13.9 g of 2-ethyl-4-methoxy-1H-indole.

| Analysis for C$_{11}$H$_{13}$NO: | |
| --- | --- |
| Calculated: | C, 75.40; H, 7.48; N, 7.99; |
| Found: | C, 74.41; H, 7.64; N, 7.97. |

Part B. Preparation of 2-Ethyl-4-methoxy-1-(phenylmethyl)-1H-indole

2-Ethyl-4-methoxy-1H-indole (4.2 g, 24 mmol) is dissolved in 30 mL of DMF and 960 mg (24 mmol) of 60% NaH/mineral oil is added. After 1.5 hours, 2.9 mL (24 mmol) of benzyl bromide is added. After 4 hours, the mixture is diluted with water extracting twice with ethyl acetate. The combined ethyl acetate is washed with brine, dried (MgSO$_4$) and concentrated at reduced pressure. The residue is chromatographed on silica gel and eluted with 20% EtOAc/hexane to give 3.1 g (49% yield) of 2-ethyl-4-methoxy-1-(phenylmethyl)-1H-indole.

Part C. Preparation of 2-Ethyl-4-hydroxy-1-(phenylmethyl)-1H-indole

A solution of 3.1 g (11.7 mmol) of 2-ethyl-4-methoxy-1-(phenylmethyl)-1H-indole and 48.6 mL of 1M BBr$_3$/CH$_2$Cl$_2$ in 50 mL of methylene chloride is stirred at room temperature for 5 hours and concentrated at reduced pressure. The residue is dissolved in ethyl acetate, washed with brine and dried (MgSO$_4$). After concentrating at reduced pressure, the residue is chromatographed on silica gel eluting with 20% EtOAc/hexane to give 1.58 g (54% yield) of 2-ethyl-4-hydroxy-1-(phenylmethyl)-1H-indole, mp, 86–90° C.

| Analysis for C$_{17}$H$_{17}$NO: | |
| --- | --- |
| Calculated: | C, 81.24; H, 6.82; N, 5.57; |
| Found: | C, 81.08; H, 6.92; N, 5.41. |

Part D. Preparation of [[2-Ethyl-1-(phenylmethyl)-1H-indol-4-yl]oxy]acetic acid tert-butyl ester 2-Ethyl-4-hydroxy-1-(phenylmethyl)-1H-indole (5.82 g, 20 mmol) is added to 7.82 g (24 mmol) cesium carbonate in 25 mL DMF and the mixture is stirred at 35° C. for 30 minutes. After cooling to 20° C., a solution of tert-butyl bromoacetate (4.65 g, 23.8 mmol) in 5 mL DMF is added and stirring maintained until the reaction is judged complete by TLC analysis (several hours). The mixture is diluted with water and extracted with ethyl acetate. The ethyl acetate solution is washed with brine, dried (MgSO$_4$) and concentrated at reduced pressure to give 6.8 g of solid. Mass spectrum: 365

| Analyses for C$_{23}$H$_{27}$NO$_3$: | |
| --- | --- |
| Calculated: | C, 75.59; H, 7.75; N, 3.83; |
| Found: | C, 75.87; H, 7.48; N, 3.94. |

Part E. Preparation of [[2-Ethyl-1-(phenylmethyl)-3-ureido-1H-indol-4-yl]oxy]acetic acid tert-butyl ester A solution of 2.3 g (6.3 mmol) [[2-ethyl-1-(phenylmethyl)-1H-indol-4-yl]oxy]acetic acid tert-butyl ester and 4.8 g (12.6 mmol) bis(2,2,2-trichloroethyl)-azodicarboxylate in diethyl ether is stirred for 24 hours at room temperature. The resulting solid is filtered and vacuum dried. This adduct (1 g, 1.3 mmol) is dissolved in 10 mL of THF and treated with zinc (1 g) and glacial acetic acid (0.5 mL). After stirring for 30 minutes at room temperature an excess of trimethyisiiyiisocyanate in 1 mL, of THF is added and stirring is continued at room temperature for 18 hours. The mixture is diluted with water and extracted with ethyl acetate. The organic layer is washed with brine, dried over MgSO$_4$ and concentrated to dryness to give 0.385 g (69% yield) of the subtitled material. Mass spectrum: 423.

| Analyses for C$_{24}$H$_{29}$N$_3$O$_4$: | |
| --- | --- |
| Calculated: | C, 68.07; H, 6.90; N, 9.92; |
| Found: | C, 67.92; H, 6.84; N, 9.70. |

Part F. Preparation of [[3-(2-Amino-1,2-dioxoethyl)-2-ethyl-1-(phenylmethyl)-1H-indol-4-yl]oxy]acetic acid A mixture of 788 mg (2 mmol) of [3-(2-amino-1,2-dioxoethyl)-2-ethyl-1-(phenylmethyl)-1H-indol-4-yl]oxy] acetic acid methyl ester, 10 mL, of in NaOH and 30 mnL of MeOH is heated to maintain ref lux for 0.5 hour, stirred at room temperature for 0.5 hour and concentrated at reduced pressure. The residue is taken up in ethyl acetate and water, the aqueous layer separated and made acidic to pH 2–3 with 1N HCl. The precipitate is filtered and washed with ethyl acetate to give 559 mg (74% yield) of [[3-(2-amino-1,2-dioxoethyl)-2-ethyl-1-(phenylmethyl)-1H-indol-4-yl]oxy] acetic acid, mp, 230–234° C.

| Analyses for C$_{21}$H$_{20}$N$_2$O$_5$: | |
| --- | --- |
| Calculated: | C, 65.96; H, 5.80; N, 7.33; |
| Found: | C, 66.95; H, 5.55; N, 6.99. |

Proportion and Weight of Active Compound in Formulations Used in the Method of the Invention The 1H-indole-3-glyoxylamide compound (as described above) may be used at a concentration of 0.1 to 99.9 weight percent of the formulation.

Preferably the pharmaceutical formulation is in unit dosage form. The unit dosage form can be a capsule or tablet itself, or the appropriate number of any of these. The quantity of active compound in a unit dose of composition may be varied or adjusted from about 0.1 to about 1000 milligrams or more according to the particular treatment involved.

Compositions (dosage forms) suitable for internal administration typically contain from about 1 milligram to about 500 milligrams of active compound per unit. In these pharmaceutical compositions the active compound will ordinarily be present in an amount of about 0.5–95% by weight based on the total weight of the composition.

The Method of the Invention—Formulation and Delivery

The sPLA$_2$ inhibitors used in the method of the invention may be administered to treat Alzheimer's disease by any means that produces contact of the active compound with the agent's site of action in the human body. The sPLA$_2$ inhibitors can be administered alone, but are generally administered with a pharmaceutical carrier selected on the basis of the chosen route of administration and standard pharmaceutical practice.

Suitable formulations are those comprising; a therapeutically effective amount of sPLA$_2$ inhibitor together with a pharmaceutically acceptable diluent or carrier, the composition being adapted for the particular route of administration chosen. By "pharmaceutically acceptable" it is meant the carrier, diluent or excipient must be compatible with the sPLA$_2$ inhibitor ("active compound") in the formulation and not deleterious to the subject being treated.

For the pharmaceutical formulations any suitable carrier known in the art can be used. In such a formulation, the carrier may be a solid, liquid, or mixture of a solid and a liquid. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc. In tablets the sPLA$_2$ inhibitor is mixed with a carrier having the necessary binding properties in suitable proportions and compacted in the shape and size desired.

Sterile liquid form formulations include suspensions, emulsions, syrups and elixirs. The active compound can be dissolved or suspended in a pharmaceutically acceptable carrier, such as sterile water, saline, dextrose solution, sterile organic solvent or a mixture of both.

The active compound can be administered orally in solid dosage forms, such as capsules, tablets, and powders, or in liquid dosage forms, such as elixirs, syrups, and suspensions. It can also be administered parenterally, in sterile liquid dosage forms. It can also be administered by inhalation in the form of a nasal spray or lung inhaler. It can also be administered topically as an ointment, cream, gel, paste, lotion, solution, spray, aerosol, liposome, or patch. Dosage forms used to administer the active compound usually contain suitable carriers, diluents, preservatives, or other excipients, as described in Remington's Pharmaceutical Sciences, Mack Publishing Company, a standard reference text in the field.

Gelatin capsules may be prepared containing the active compound and powdered carriers, such as lactose, sucrose, mannitol, starch, cellulose derivatives, magnesium stearate, stearic acid, and the like. Similar diluents can be used to make compressed tablets and powders. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

For parenteral solutions, water, a suitable oil, saline, aqueous dextrose (glucose), and related sugar solutions and glycols such as propylene glycol or polyethylene glycols are suitable carriers for parenteral solutions. Solutions for parenteral administration contain the active compound, suitable stabilizing agents, and if necessary, buffer substances. Anti-oxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

Topical ointments, creams, gels, and pastes contain with the active compound diluents such as waxes, paraffins, starch, polyethylene glycol, silicones, bentonites, silicic acid, animal and vegetable fats, talc and zinc oxide or mixtures of these or other diluents.

Topical solutions and emulsions can, for example, contain with the active compound, customary diluents (with the exclusion of solvents having a molecular weight below 200 except in the presence of a surface-active agent), such as solvents, dissolving agents and emulsifiers; specific examples are water, ethanol, 2-propanol, ethyl carbonate, benzyl alcohol, propylene glycol, oils, glycerol, and fatty acid esters of sorbitol or mixtures thereof. Compositions for topical dosing may also contain preservatives or anti-oxidizing agents.

Powders and sprays can contain along with the active compound, the usual diluents, such as lactose, talc, silicic acid, aluminum hydroxide, calcium silicate, and polyamide powders or mixtures of these materials. Aerosol sprays can contain the usual propellants. Liposomes can be made from such materials as animal or vegetable fats which will form lipid bilayers in which the active compound can be incorporated.

Formulations containing compounds of the invention may be administered through the skin by an appliance such as a transdermal patch. Patches can be made of a matrix such as polyacrylamide and a semipermeable membrane made from a suitable polymer to control the rate at which the material is delivered to the skin. Other suitable transdermal patch formulations and configurations are described in U.S. Pat. Nos. 5,296,222 and 5,271,940, the disclosures of which are incorporated herein by reference. Lipophilic prodrug derivatives of the sPLA$_2$ inhibitors are particularly well suited for transdermal absorption administration and delivery systems.

Formulations within the scope of this invention include the admixture of sPLA2 inhibitor with a other therapeutically effective co-agents for treatment of Alzheimer's disease.

For all of the above formulations the preferred active compound are the 1H-indole-3-glyoxylamide compounds as previously described (e.g., Formula I) and methods of making as described in U.S. Pat. No. 5,654,326 (the disclosure of which is incorporated herein by reference). Most preferred compounds within the general class of 1H-indole-3-glyoxylamides are ((3-(2-amino-1,2-dioxoethyl)-2-ethyl-1-(phenylmethyl)-1H-indol-4yl)oxy)acetic acid, sodium salt; and 1H-indole-3-glyoxylamides are ((3-(2-amino-1,2-dioxoethyl)-2-ethyl-1-(phenylmethyl)-1H-indol-4yl)oxy) acetic acid, methyl ester.

The Practice of the Method of the Invention

Treatment of Alzheimer's disease in a human may be therapeutic by administering a 1H-indole-3-glyoxylamide sPLA$_2$ inhibitor to treat an existing condition or prophylactic by administering a 1H-indole-3-glyoxylamide sPLA$_2$ inhibitor in anticipation of Alzheimer's disease, for example, in a patient whose age, lifestyle, or family history is predictive of the disease.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

In general, the sPLA$_2$ inhibitor will be administered to a human so that an effective amount is received. An effective amount may conventionally be determined for an individual patient by administering the active compound in increasing doses and observing the effect on the patient, for example, maintenance of memory and cognitive abilities.

Generally, the compound will typically be administered in a manner and a dose to achieve in the human a blood level concentration of sPLA$_2$ inhibitor of from 100 to 5000 nanograms/ml, and preferably a concentration of 250 to 600 nanograms/ml.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Alternatively, the delivery of hydrophilic drugs may be enhanced by intra-arterial infusion of hypertonic solutions which can transiently open the blood-brain barrier.

The treatment regimen for many Alzheimer's disease may stretch over many years for the remaining life of the patient. Oral dosing is preferred for patient convenience and tolerance. With oral dosing, one to four oral doses per day, each from about 0.01 to 25 mg/kg of body weight with preferred doses being from about 1 mg/kg to about 5 mg/kg.

Parenteral administration (particularly, intravenous administration) is often preferred in instances where rapid alleviation of patient distress is required. With parenteral administration doses of about 0.1 to about 25 mg/kg/day administered continuously or intermittently throughout the day may be used. For parenteral administation, the compound may be administered in a physiologic saline vehicle (e.g., 0.9% normal saline, 0.45% normal saline, etc.) a dextrose vehicle (e.g., 5% dextrose in water), or a combination of saline and dextrose vehicle (0.9% normal saline in 5% dextrose).

Inhalation therapy also may be useful either alone or as an adjunct to other routes of administration. With inhalation therapy, doses necessary to produce a decrease in the clinical symptoms of Alzheimer's disease are used.

Testing Methods for Alzheimer's Disease

The diagnostic criteria for Alzheimer's disease are those found in standard medical references (e.g., Harrison's Principles of Internal Medicine, thirteenth ed., 1994, by McGraw-Hill, Inc., ISBN 0-07-032370-4, pgs., 2270–2272). These criteria may be used to determine when to begin using the method of the invention, the frequency and degree of treatment.

A Suitable Assay Protocol for Alzheimer's Disease is found in U.S. Pat. No. 5,686,269 (the disclosure of which is incorporated herein by reference) and may be employed in determining the beginning, duration, and end of treatment by the method of this invention as set out below:

Criteria for the clinical diagnosis of probable Alzheimer's disease include dementia established by clinical examination and documented by the Mini-Mental State Examination, Blessed Dementia Scale, or some similar examination and confirmed by neuropsychologic tests:

a. Deficits in two or more areas of cognition.

b. Progressive worsening of memory and other cognitive functions.

c. No disturbance of consciousness.

d. Onset between ages 40 and 90.

e. Absence of systemic disorders or other brain diseases that could account for the progressive deficits in memory and cognition.

The diagnosis of probable Alzheimer's disease is supported by;

a. Progressive deterioration of specific cognitive functions such as language (aphasia), motor skills (apraxia), and perception (agnosia).

b. Impaired activities of daily living and altered patterns of behavior.

c. Family history of similar disorders, particularly if confirmed neuropathologically.

d. Laboratory results as follows: normal lumbar puncture as evaluated by standard techniques; normal pattern or nonspecific changes in EEG, such as increased slow-wave activity; and evidence of cerebral atrophy on CT with progression documented by serial observation.

Other clinical features consistent with the diagnosis of probable Alzheimer's disease, after exclusion of causes of dementia other than Alzheimer's disease, include;

Plateaus in the course of progression of the illness.

Associated symptoms of depression, insomnia, incontinence, delusions, illusions, hallucinations, sexual disorders, weight loss, and catastrophic verbal, emotional, or physical outbursts.

Other neurologic abnormalities in some patients, especially with more advanced disease and including motor signs such as increased muscle tone, myoclonus, or gait disorder.

Seizures in advanced disease

CT normal for age

Features that make the diagnosis of probable Alzheimer's disease uncertain or unlikely include:

a. Sudden, apoplectic onset.

b. Focal neurologic findings such as hemiparesis, sensory loss, visual field deficits, and in coordination early in the course of the illness.

c. Seizures or gait disturbances at the onset or very early in the course of the illness.

Clinical diagnosis of possible Alzheimer's disease may be on the basis of the dementia syndrome, in the absence of other neurologic, psychiatric, or systemic disorders sufficient to cause dementia and in the presence of variations in the onset, presentation, or clinical course.

Clinical diagnosis of possible Alzheimer's disease may also be made in the presence of a second systemic or brain disorder sufficient to produce dementia such as a. Familial occurrence b. Onset before age 65 c. Presence of trisomy 21 d. Coexistence of other relevant conditions, such as Parkinson's disease nNote:

nNINCDS=National Institute of Neurological and Communicative Disorders and Stroke;

nADRDA=Alzheimer's Disease and Related Disorders Association

Under the current standards established by the Consortium to Establish a Registry for Alzheimer's Disease (CERAD), a post-mortem diagnosis of definite AD involves a series of histopathologic tests on biological samples obtained from the patient.

Another suitable Assay Protocol for Alzheimer's Disease is found in U.S. Pat. No. 5,686,476 (the disclosure of which is incorporated herein by reference) and may be employed in determining the beginning, duration, and end of treatment by the method of this invention as set out below:

Five to fifty women are selected for the clinical study. The women are post-menopausal, i.e., have ceased menstruating for between 6 and 12 months prior to the study's initiation, have been diagnosed with early stage Alzheimer's Disease (AD), are expected to have worsening symptoms of AD within the study period, but are in good general health otherwise. The study has a placebo control group, i.e., the women are divided into two groups, one of which receives the active agent of this invention and the other receives a placebo.

The patients are benchmarked as to memory, cognition, reasoning, and other symptoms associated with AD. Women in the test group receive a therapeutically effective dose of sPLA2 inhibitor each day. They continue this therapy for 6–36 months. Accurate records are kept as to the benchmarked symptoms in both groups and at the end of the study these results are compared. The results are compared both between members of each group and also the results for each patient are compared to the symptoms reported by each patient before the study began. Activity of the test drug is illustrated by an attenuation of the typical cognitive decline and/or behavioral disruptions associated with AD.

Utility of the sPLA2 inhibitor compounds for treatment of Alzheimer's disease is evidenced by activity in this assay protocol.

While the present invention has been illustrated above by certain specific embodiments, these are not intended to limit the scope of the invention as described in the appended claims.

I claim:

1. A method for the prophylactic or therapeutic treatment of a mammal afflicted with Alzheimer's disease, said method comprising administering to a mammal in need thereof, an effective amount of a 1H-indole-3-glyoxylamide type sPLA$_2$ inhibitor.

2. A method for treating a human susceptible to having Alzheimer's disease to prevent or delay the onset of Alzheimer's disease; said method comprising administering to said human in need thereof a prophylactically effective amount of a 1H-indole-3-glyoxylamide sPLA$_2$ inhibitor represented by the formula (I), or a pharmaceutically acceptable salt or aliphatic ester prodrug derivative thereof;

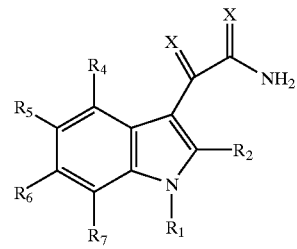
(I)

wherein;

both X are oxygen;

$R_1$ is selected from the group consisting of

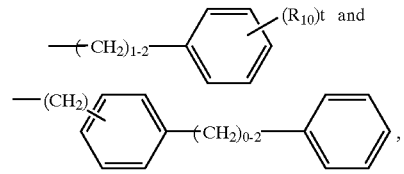

where $R_{10}$ is a radical independently selected from halo, $C_1$–$C_{10}$ alkyl, $C_1$–$C_{10}$ alkoxy, —S—($C_1$–$C_{10}$ alkyl), and $C_1$–$C_{10}$ haloalkyl and t is a number from 0 to 5;

$R_2$ is selected from the group; halo, cyclopropyl, methyl, ethyl, and propyl;

$R_4$ and $R_5$ are independently selected from hydrogen, a non-interfering substituent, or the group, —($L_a$)-(acidic group); wherein —($L_a$)— is an acid linker; provided, the acid linker group, —($L_a$)—, for $R_4$ is selected from the group consisting of;

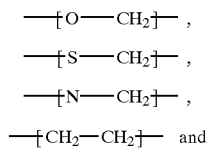

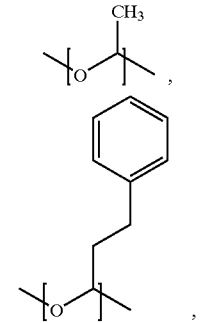

and provided, the acid linker, —($L_a$)—, for $R_5$ is selected from group consisting of;

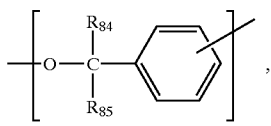

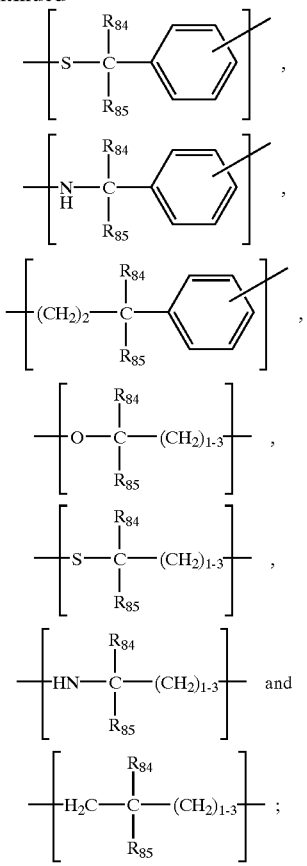

wherein $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo; and provided, that at least one of $R_4$ and $R_5$ must be the group, —($L_a$)-(acidic group) and wherein the (acidic group) on the group —($L_a$)-(acidic group) of $R_4$ or $R_5$ is selected from —$CO_2H$, —$SO_3H$, or —$P(O)(OH)_2$;

$R_6$ and $R_7$ are each independently selected form hydrogen and non-interfering substituents, with the non-interfering substituents being selected from the group consisting of the following: $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_2$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —C(O)O($C_1$–$C_6$ alkyl), —$(CH_2)_n$—O—($C_1$–$C_6$ alkyl), benzyloxy, phenoxy, phenylthio, —(CONHSO$_2$R), —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and $C_1$–$C_6$ carbonyl; where n is from 1 to 8.

3. The method of claim 2 wherein the 1H-indole-3-glyoxylamide sPLA$_2$ inhibitor or a pharmaceutically acceptable salt, solvate, or a prodrug derivative thereof is selected from the group consisting of compounds (A) through (P):

(A) [[3-(2-Amino-1,2-dioxoethyl)-2-methyl-1-(phenylmethyl)-1H-indol-4-yl]oxy]acetic acid, (B) d-2-[[3-(2-Amino-1,2-dioxoethyl)-2-methyl-1-(phenylmethyl)-1H-indol-4-yl]oxy]propanoic acid, (C) [[3-(2-Amino-1,2-dioxoethyl)-1-([1,1'-biphenyl]-2-ylmethyl)-2-methyl-1H-indol-4-yl]oxy]acetic acid, (D) [[3-(2-Amino-1,2-dioxoethyl)-1-([1,1'-biphenyl]-3-ylmethyl)-2-methyl-1H-indol-4-yl]oxy]acetic acid, (E) [[3-(2-Amino-1,2-dioxoethyl)-1-([1,1'-biphenyl]-4-ylmethyl)-2-methyl-1H-indol-4-yl]oxy]acetic acid, (F) [[3-(2-Amino-1,2-dioxoethyl)-1-[(2,6-dichlorophenyl)methyl]-2-methyl-1H-indol-4-yl]oxy]acetic acid (G) [[3-(2-Amino-1,2-dioxoethyl)-1-[4(-fluorophenyl)methyl]-2-methyl-1H-indol-4-yl]oxy]acetic acid, (H) [[3-(2-Amino-1,2-dioxoethyl)-2-methyl-1-[(1-naphthalenyl)methyl]-1H-indol-4-yl]oxy]acetic acid, (I) [[3-(2-Amino-1,2-dioxoethyl)-2-ethyl-1-(phenylmethyl)-1H-indol-4-yl]oxy]acetic acid, (J) [[3-(2-Amino-1,2-dioxoethyl)-1-[(3-chlorophenyl)methyl]-2-ethyl-1H-indol-4-yl]oxy]acetic acid, (K) [[3-(2-Amino-1,2-dioxoethyl)-1-([1,1'-biphenyl]-2-ylmethyl)-2-ethyl-1H-indol-4-yl]oxy]acetic acid, (L) [[3-(2-amino-1,2-dioxoethyl)-1-([1,1'-biphenyl]-2-ylmethyl)-2-propyl-1H-indol-4-yl]oxy]acetic acid, (M) [[3-(2-Amino-1,2-dioxoethyl)-2-cyclopropyl-1-(phenylmethyl)-1H-indol-4-yl]oxy]acetic acid, (N) [[3-(2-Amino-1,2-dioxoethyl)-1-([1,1'-biphenyl]-2-ylmethyl)-2-cyclopropyl-1H-indol-4-yl]oxy]acetic acid, (O) 4-[[3-(2-Amino-1,2-dioxoethyl)-2-ethyl-1-(phenylmethyl)-1H-indol-5-yl]oxy]butanoic acid, and (P) mixtures of (A) through (O).

4. The method of claim 2 wherein 1H-indole-3-glyoxylamide sPLA$_2$ inhibitor is selected from the group consisting of compounds represented by the formulae:

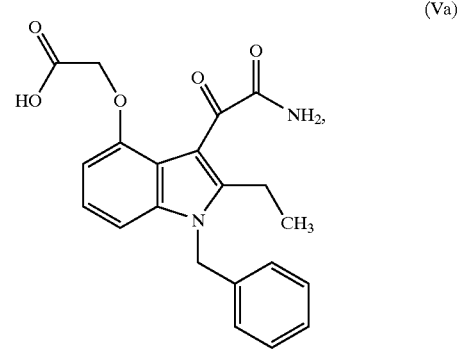

(Va)

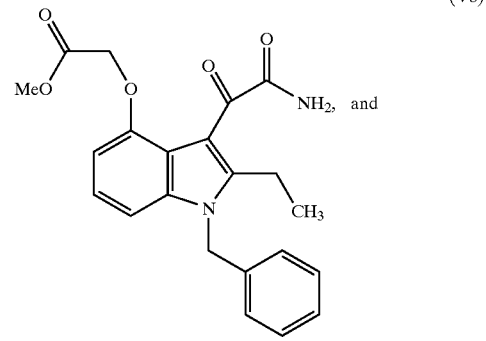

(Vb)

-continued

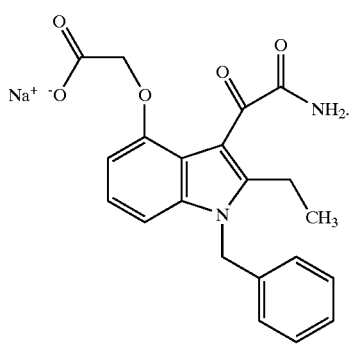
(Vc)

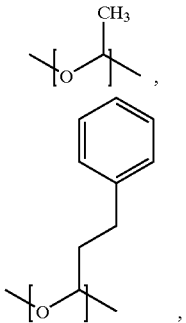

5. A method for treating a human afflicted with Alzheimer's disease to prevent or diminish the rate of further deterioration; said method comprising administering to said human a therapeutically effective amount of a 1H-indole-3-glyoxylamide sPLA$_2$ inhibitor represented by the formula (I), or a pharmaceutically acceptable salt or aliphatic ester prodrug derivative thereof;

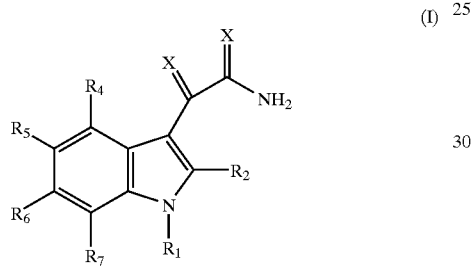
(I)

wherein;
both X are oxygen;
$R_1$ is selected from the group consisting of

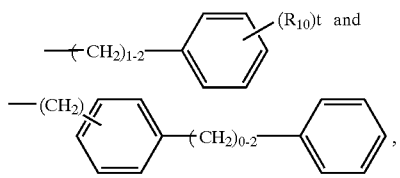

where $R_{10}$ is a radical independently selected from halo, $C_1$–$C_{10}$ alkyl, $C_1$–$C_{10}$ alkoxy, —S—($C_1$–$C_{10}$ alkyl), and $C_1$–$C_{10}$ haloalkyl and t is a number from 0 to 5;

$R_2$ is selected from the group; halo, cyclopropyl, methyl, ethyl, and propyl;

$R_4$ and $R_5$ are independently selected from hydrogen, a non-interfering substituent, or the group, —($L_a$)-(acidic group); wherein —($L_a$)— is an acid linker; provided, the acid linker group, —($L_a$)—, for $R_4$ is selected from the group consisting of;

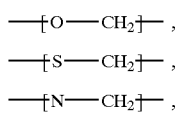

and provided, the acid linker, —($L_a$)—, for $R_5$ is selected from group consisting of;

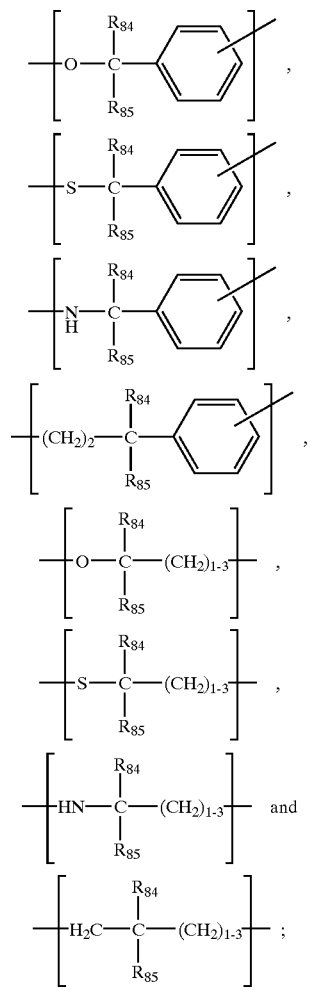

wherein $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo; and provided, that at least one of $R_4$ and $R_5$ must be the group, —($L_a$)-(acidic group) and wherein the (acidic group) on the group —($L_a$)-(acidic group) of $R_4$ or $R_5$ is selected from —$CO_2H$, —$SO_3H$, or —$P(O)(OH)_2$;

$R_6$ and $R_7$ are each independently selected form hydrogen and non-interfering substituents, with the non-interfering substituents being selected from the group consisting of the following: $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_2$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —C(O)O($C_1$–$C_6$ alkyl), —(CH$_2$)$_n$—O—($C_1$–$C_6$ alkyl), benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and $C_1$–$C_6$ carbonyl; where n is from 1 to 8.

6. The method of claim 5 wherein the 1H-indole-3-glyoxylamide sPLA$_2$ inhibitor or a pharmaceutically acceptable salt, solvate, or a prodrug derivative thereof is selected from the group consisting of compounds (A) through (P):

(A) [[3-(2-Amino-1,2-dioxoethyl)-2-methyl-1-(phenylmethyl)-1H-indol-4-yl]oxy]acetic acid,
(B) d-2-[[3-(2-Amino-1,2-dioxoethyl)-2-methyl-1-(phenylmethyl)-1H-indol-4-yl]oxy]propanoic acid,
(C) [[3-(2-Amino-1,2-dioxoethyl)-1-([1,1'-biphenyl]-2-ylmethyl)-2-methyl-1H-indol-4-yl]oxy]acetic acid,
(D) [[3-(2-Amino-1,2-dioxoethyl)-1-([1,1'-biphenyl]-3-ylmethyl)-2-methyl-1H-indol-4-yl]oxy]acetic acid,
(E) [[3-(2-Amino-1,2-dioxoethyl)-1-([1,1'-biphenyl]4-ylmethyl)-2-methyl-1H-indol-4-yl]oxy]acetic acid,
(F) [[3-(2-Amino-1,2-dioxoethyl)-1-[(2,6-dichlorophenyl)methyl]-2-methyl-1H-indol-4-yl]oxy]acetic acid
(G) [[3-(2-Amino-1,2-dioxoethyl)-1-[4(-fluorophenyl)methyl]-2-methyl-1H-indol-4-yl]oxy]acetic acid,
(H) [[3-(2-Amino-1,2-dioxoethyl)-2-methyl-1-[(1-naphthalenyl)methyl]-1H-indol-4-yl]oxy]acetic acid,
(I) [[3-(2-Amino-1,2-dioxoethyl)-2-ethyl-1-(phenylmethyl)-1H-indol-4-yl]oxy]acetic acid,
(J) [[3-(2-Amino-1,2-dioxoethyl)-1-[(3-chlorophenyl)methyl]-2-ethyl-1H-indol-4-yl]oxy]acetic acid,
(K) [[3-(2-Amino-1,2-dioxoethyl)-1-([1,1'-biphenyl]-2-ylmethyl)-2-ethyl-1H-indol-4-yl]oxy]acetic acid,
(L) [[3-(2-amino-1,2-dioxoethyl)-1-([1,1'-biphenyl]-2-ylmethyl)-2-propyl-1H-indol-4-yl]oxy]acetic acid,
(M) [[3-(2-Amino-1,2-dioxoethyl)-2-cyclopropyl-1-(phenylmethyl)-1H-indol-4-yl]oxy]acetic acid,
(N) [[3-(2-Amino-1,2-dioxoethyl)-1-([1,1'-biphenyl]-2-ylmethyl)-2-cyclopropyl-1H-indol-4-yl]oxy]acetic acid,
(O) 4-[[3-(2-Amino-1,2-dioxoethyl)-2-ethyl-1-(phenylmethyl)-1H-indol-5-yl]oxy]butanoic acid, and
(P) mixtures of (A) through (O).

7. The method of claim 5 wherein 1H-indole-3-glyoxylamide sPLA$_2$ inhibitor is selected from the group consisting of compounds represented by the formulae:

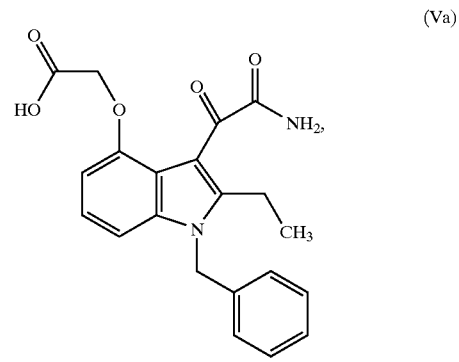
(Va)

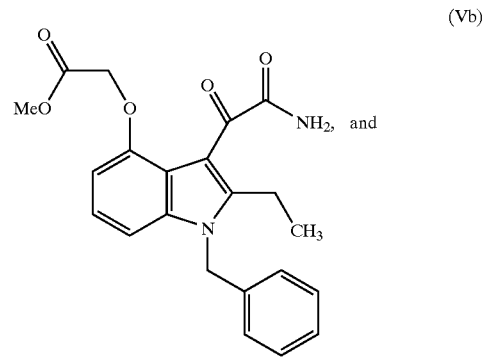
(Vb)

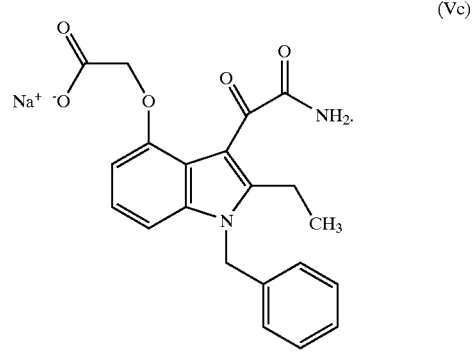
(Vc)

* * * * *